United States Patent [19]

Davidson

[11] Patent Number: 5,811,526
[45] Date of Patent: *Sep. 22, 1998

[54] BINDING ASSAY AND ASSAY REAGENT

[75] Inventor: Robert Stephen Davidson, Leicester, England

[73] Assignee: Alusuisse Holdings A.G., Neuhausen am Rheinfall, Switzerland

[*] Notice: The term of this patent shall not extend beyond the expiration date of Pat. No. 5,585,279.

[21] Appl. No.: 447,847

[22] Filed: May 23, 1995

Related U.S. Application Data

[63] Continuation of Ser. No. 287,588, Aug. 8, 1994, Pat. No. 5,585,279, which is a continuation of Ser. No. 837,089, Feb. 18, 1992, abandoned, which is a continuation of Ser. No. 121,750, filed as PCT/GB97/00040, Jan. 23, 1987, abandoned.

[30] Foreign Application Priority Data

Jan. 23, 1986 [GB] United Kingdom .................. 8601646

[51] Int. Cl.$^6$ ........................ E07K 16/00; G01N 33/532
[52] U.S. Cl. ...................... 530/391.3; 530/345; 530/402; 435/7.1; 532/136; 546/2; 546/10
[58] Field of Search ............................. 435/7.1; 436/518, 436/526, 537, 543, 546, 164, 172, 800, 805; 530/345, 391.3, 391.5, 402; 532/136; 546/2, 10

[56] References Cited

U.S. PATENT DOCUMENTS

| | | | |
|---|---|---|---|
| 4,205,952 | 6/1980 | Cais ......................................... | 436/518 |
| 4,293,310 | 10/1981 | Weber ...................................... | 436/536 |
| 4,372,745 | 2/1983 | Mandle et al. ........................... | 436/537 |
| 4,432,907 | 2/1984 | Weider et al. ........................... | 436/546 |
| 4,656,143 | 4/1987 | Baker et al. ............................. | 436/527 |
| 4,745,076 | 5/1988 | Müller et al. ............................ | 436/537 |
| 5,221,605 | 6/1993 | Bard et al. ................................ | 435/4 |

FOREIGN PATENT DOCUMENTS

| | | |
|---|---|---|
| 0064484 | 11/1982 | European Pat. Off. . |
| 0178450 | 4/1986 | European Pat. Off. . |
| 2353854 | 12/1977 | France . |
| 84/03698 | 9/1984 | WIPO . |
| 86/02734 | 5/1986 | WIPO . |

OTHER PUBLICATIONS

Bard et al., *Chemical Abstracts*, 107(19): 172003x, (1987).
Buckingham, D.A. et al., "Mono–and bis–(2,2'–bipyridine) and (1,10)–phenanthroline) Chelates of Ruthenium and Osmium", *Australian Journal of Chemistry*, vol. 17, pp. 325–336 (1964).
Cais et al., *Nature*, 270: 534–535, (1977).
Divisia et al., *Journal of American Chemical Society*, vol. 102, No. 24, pp. 7264–7268, (1980).
Hemmilä, I., "Fluoroimmunoassays and Immunofluorometric Assays", *Clinical Chemistry*, vol. 31, No. 3, pp. 359–370, Mar. 1985.
Kahl, J.L. et al., "Preparation and Identification of Iridium Bipyridine and Phenanthroline Complexes", *Journal of Inorganic and Nuclear Chemistry*, vol. 41, pp. 495–502 (1979).
Kirk et al., "Luminescence of Chromium(III) Complexes", *Journal of Physical Chemistry*, 84: 887–891, (1980).
Stone, M.L. et al., "Charge Transfer Luminscence from Ruthenium(II) Complexes Containing Tridentate Ligands", *Chemical Abstracts*, vol. 94, No. 26, p. 551, abstract 216784x, and Chem. Phys. Lett. 79(1) pp. 167–173 (1981).

*Primary Examiner*—Lora M. Green
*Attorney, Agent, or Firm*—Spencer & Frank

[57] ABSTRACT

A time-resolving luminescence binding assay involves a metal-labelled binding partner comprising a luminescent transition metal complex covalently attached to a binding partner such as an antigen or antibody. Ruthenim, iridium, osmium, and chromium luminescent complexes are described.

5 Claims, No Drawings

BINDING ASSAY AND ASSAY REAGENT

This is a Continuation of application Ser. No. 08/287,588 filed Aug. 8, 1994; now U.S. Pat. No. 5,589,279, which is a continuation of application Ser. No. 07/837,089, filed Feb. 18, 1992, now abandoned, which is a continuation of application Ser. No. 07/121,750, filed as PCT/GB97/00040, Jan. 23, 1987, now abandoned.

The present invention relates to a time-resolved luminescence binding assay, and to reagents for use therein.

Time-resolved luminescence binding assays are known.

British patent specification 1560402 (Analytical Radiation Corporation) describes the use of fluorescent labels in immunoassay and in particular, the use of labels with a relatively long fluorescence life time. In this way, fluorescence from the labels can be distinguished from relatively short-lived competing fluorescence from the sample, assay reagents and the like, thus improving the signal-to-noise ratio of the assay. The specific labels referred to are organic fluorescent compounds represented by pyrenebutyrate and rare-earth chelates, especially chelates of europium and terbium.

Published European patent specification EP-A2-0103558 (Wallac Oy) describes a homogeneous time-resolved fluorescence immunoassay in which an immunochemical compound labelled with a lanthanide chelate us used, the labelled compound exhibiting a fluorescence, the characteristics of which are modulated by binding of the immunochemical compound to a specific binding partner.

The known techniques of time-resolved fluorescence immunoassay rely to a very terbium (Tb (III)). These metals form highly fluorescent chelates, each exhibiting a long fluorescence life time (100 to 1,000 us), a broad excitation bandwidth, a large Stokes shift (difference between excitation and emission wave lengths—typically greater than 250 nm) and a narrow emission bandwidth. The fluorescence life time of the rare-earth chelates is several orders of magnitude greater than the average background fluorescence encountered in, say a biological sample (typically 1 to 20 ns). The rare-earth chelates do however suffer from several disadvantages. They are kinetically labile and susceptible to the quenching and dissociative properties of water.

These disadvantages have led to considerable research into the stabilisation of rare-earth chelates and improved protocols for their use. International published patent application WO 84/03698 describes an improved chelating compound for inter alia lanthanides. European published patent application EP-A2-0064484 describes a protocol in which a lanthanide ion is caused to dissociate from a non-fluorescent chelate bound to a component of the assay. The lanthanide ion subsequently forms a highly fluorescent chelate with a chelating agent such as a β-diketone in solution. United States patent specification 4374120 describes a chelating agent for europium of terbium comprising a β-diketone or a dihydroxy compound, and an aminopolycarboxylic acid analogue.

For a general review of fluoroimmunoassays see Hemmila, I. Clin. Chem. (1985) 31(3) 359–370.

It has been recognized that the prior art rare-earth metal chelate labels are not completely satisfactory. The prior art indicates that considerable efforts have been made to improve the stability of the rare-earth chelates, but instability is still a problem as is the cost and toxicity of the reagents.

Fluorescent transition metal complexes having the requisite luminescence decay properties are known to be stable. In particular luminescent osmium and ruthenium complexes have been studies extensively (see for example, Ackermann et al Inor. Chem. (1984) 23 3904–3911). These studies have been confined to their unusual excited states properties and their potential use a photosensitisors in of solar energy. U.S. Pat. No. 4,205,952 describes the use of metal labels in binding assays. The specification relates in particular to the use of atomic absorpotion to detect and measure the metal labels. The use of transition metals and their complexes are broadly disclosed. It has been discovered that such transition metal complexes are emninently suited to use in time-resolved luminescence immunoassay.

European patent application EP-A2-0178450 (published 23rd Apr., 1986) described various ruthenium complexes attached to immunologically active material, for use in time-resolved fluorescence immunoassay.

According to the present invention, there is provided a time-resolved luminescence binding assay method involving a metal-labelled binding partner characterised in that the metal label comprises a luminescent transition metal complex.

The metal label comprises a transition metal complexed with one or more ligands. At least one of the ligands is provided with a chemical linkage covalently binding the ligand (and hence the complex) to the binding partner.

The luminescent transition metal complex is selected to exhibit a luminescence having a life-time substantially longer than that of the background luminescence of the assay environment. In a typical immunoassay carried out on a biological sample, the life-time of the luminescence is suitably longer than 20 ns. Preferably the life-time is longer than 100 ns and is up to 5 $\mu$s. The luminescence exhibited by the complex may be fluorescence or phosphorescence or a combination of the two phenomena.

The transition metal is a d-block elements selected from one of the three rows of d-blocks elements in the periodic table, and which, in a complex, exhibits the requisite luminescence property. For the avoidance of doubt, the term "transition metal" as used herein specifically excludes the lanthanide and actinide elements. Ruthenium and iridium are particularly preferred especially as Ru (II) and Ir(III) respectively. Both have very good fluorescence properties. However, iridium complexes have been found to be particularly useful and have a considerably lower maximum excitation wavelengths than corresponding ruthenium complexes. This facilitates their use in laser excited fluorimeters. Other transition metals of interest include osmium, molybdenum, tungsten, chromium, indium, rhenium and rhodium, in various oxidation states, particularly osmium and chromium. Osmium is known for its high toxicity. It has however been discovered that when complexed, the level of toxicity is markedly reduced. This makes such complexes acceptable as labels in routine time-resolved flourescence binding assays.

The ligand is selected from those ligands capable of producing the necessary ligand field in the complex to render the complex luminescent. Suitable ligands include pyridine, ethylenediamine, diethylenediamine, dimethylgloxime, acetylacetonate, ethylendiamine tetraacetic acid, and the like. Preferred ligands are bipyridyls, phenanthrolines and derivatives thereof. At least one ligand is provided with a linker for covalent attachment of the complex to the binding partner. The linker may be derived from a simple reactive functional group such as a carboxyl group on the ligand or may be a diradical bridge. The bridge length may be adjusted to provide optimum performance both in terms of binding and luminescence. The bridge length is a particular significance when the assay is a homogeneous binding assay.

The binding assay may be a homogeneous binding assay or a heterogeneous binding assay. Preferably the binding assay is an immunoassay.

We have discovered that complexes of ruthenium and iridium are especially suitable for use as metal labels in time-resolved luminescence immunoassay.

According to a further aspect of the invention we provide a metal-labelled binding partner for use in a time-resolved luminescence binding assay, comprising a binding partner covalently bonded to a ruthenium or iridium luminescent complex. Preferably the ruthenium is in a II oxidation state and the iridium is a III oxidation state. The ligand may be as described above. Examples of particular metal-labelled binding partners are given below.

The binding partner is, for an immunoassay, an antigen or an antibody.

The invention is now described by way of example with reference to the following specific description.

The following abbreviations are used for certain of the ligands described:

bipy 2,2'-bipyridine
phen 1,10-phenanthroline
dpphen 4,7-diphenyl-1,10 phenanthroline
biquin 2,2'biquinoline
I 4-(p-methoxyphenyl)-1,10-phenanthroline
II 4-(p-hydroxyphenyl)-1,10-phenanthroline
III 4"-carboxybenzyl-4'-[4-(1,10-phenanthroline)] phenyl ether
IV 4'-[4-(1,10-phenanthroline)]-phenoxyacetic acid
V 4-phenyl-7-phenyl (4'-phenylacetic acid)-1,10 phenanthroline.

1. Preparation of Transition Metal Chelates

Various transition metal chelates were prepared and their fluorescence properties were measured and compared.

1.1 $Ru(bipy)_3Cl_2$ $Ru(bipy)_3Cl_2$ was prepared by first preparing $Ru(bipy)_2Cl_2$ and then adding a third bipy ligand. $RuCl_3$ $3H_2O$ (0.78 g, $2.98 \times 10^{-3}$ mol), 2,2'-dipyridyl (0.94 g, $6.0 \times 10^{-3}$ mol) and lithium chloride (0.84 g, $2.0 \times 10^{-2}$ mol) in dimethylformamide (30 ml) were heated under reflux, with stirring for 5 h. The mixture was concentrated in vacuo to approximately 5.0 ml, treated with acetone (25 ml) and cooled to 0° C. The purple-black precipitate was filtered off, washed with water (3×25 ml) and diethyl ether (2×20 ml) and dried in vacuo. (Yield 0.573 g, 37%).

A solution of bipy (0.21 g, $5.73 \times 10^{-4}$ mol) in DMF (30 ml) was added to a boiling solution of $Ru(bipy)_2Cl_2$ (0.27 g, $5.21 \times 10^{-4}$ mol) in ethanol (50 ml) and water (50 ml) and the mixture was heated under reflux for 3 hours under nitrogen. Saturated NaCl (aq) (1 ml) was added and the mixture was concentrated in vacuo to an orange solid. T.L.C. (cellulose; 2-BuOH-$H_2O$-acetic acid, 13:6:2) revealed a major orange-yellow component Rf=0.72. The mixture was chromatographed on Sephadex LH28 (Trade Mark) (ethanol) to give an orange solid (0.24, 49%).

The procedure described above for adding a third ligand to a bichelated $Ru^{2+}$ complex is generally applicable.

1.2 $Ru(phen)_3Cl_2$ $Ru(phen)_3Cl_2$ was prepared by first preparing Ru $(phen)_2Cl_2$ and then adding a third phen ligand.

$RuCl_3$ $3H_2O$ (0.78 g, $2.98 \times 10^{-3}$ mol), 1,10-phenanthroline (1.08 g, $6.0 \times 10^{-3}$ mol) and lithium chloride (0.8 μg) in dimethylforamamide (30 ml) were heated under reflux, with stirring, for 5 h. The mixture was cooled, concentrated to 5 ml in vacuo and treated with water (25 ml). The purple-black precipitate was filtered off, washed with water (2×20 ml) and diethylether (3×25 ml) and dried in vacuo. (Yield: 0.68 g, 43%).

The third phen ligand was added using the general procedure described for bipy in Section 1.1 above.

1.3 $Ir(bipy)_3 (NO_3)_3$ $Ir(bipy)_3 NO_3)_3$ was prepared following essentially the procedure described in J. Inorg. Nucl. Chem., 41, 495–502, (1979).

A 1 litre beaker containing 2.0 g of $IrCl_3$, 24.0 g of $KHSO_4$ and 20 ml of $H_2O$ was heated slowly to dryness with stirring. This mixture was heated to the melting point of $KHSO_4$(214°C.) for 30 min. with stirring (deep green) and then cooled to R.T. The iridium bisulphate melt, 24.0 g of $K_2S_2O_7$, 6.0 g of bipyridine and 20 ml of $H_2O$ were added to a new reacction flask. The temperature was held at 120° C. under an $N_2$ atmosphere until the $H_2O$ was removed. The temperature was raised to 180° C. and the $N_2$ replaced by $CO_2$. The two layered melt (one brown, one yellow) was held at 230° C. for 6 hours.

The melt was cooled to room temperature and dissolved in 200 ml $H_2O$. The pH was adjusted to 7.0 with $KHCO_3$, 800 ml of methanol added, cooled to 0° C. for 2 hours and filtered to remove $K_2SO_4$. The filtrate was flash evaporated to 90 ml, cooled to 5° C. for one hour and filtered to remove excess bipyridine. To the filtrate was added 600 ml of 0.2M $HNO_3$, flash evaporated at 70° C. to 10 ml and and at 40° C. to dryness. The yellow solid was redissolved in 600 ml of 0.2M $HNO_3$ and evaporated in vacuo as above.

The solid was dissolved in 100 ml $H_2O$, adjusted to pH 4.0 and chromatographed on Cellex-P. The column was eluted with $1 \times 10^{-4}$M $HNO_3$, 0.05M $HNO_3$, and 0.1M $HNO_3$. The 0.1M fraction was neutralised, evaporated in vacuo at 70° C. to 100 ml, checked for neutrality and evaporated in vacuo at 40° to dryness.

The solid from the 0.1M fraction was dissolved in methanol and chromatographed on Sephadex LB-20 (Trade Mark). the sample separated into 5 bands. The emission spectrum of the bright green luminescent band showed that in contained $Ir(bipy)_3^{3+}$. This band was chromatographed five additional times on Sephadex LH-10 (Trade Mark) by the above procedure. The last application on Sephadex LH-20 was done without using a UV lamp. This portion gave pale yellow crystals of $Ir(bipy)_3(NO_3)_3$ upon addition of 2-propanol and evaporation. (Yield: 50 mg).

1.4 $Ir(phen)_3(NO_3)_3$ $Ir(phen)_3(NO_3)_3$ was prepared following the general procedure described above in Section 1.3 for $Ir(bipy)_3(NO_3)_3$.

1.5 $OS(bipy)_3Cl_2$ $OS(bipy)_3Cl_2$ was prepared according to the method of Buckingham et al (Buckingham et al, Aust. J. Chem., 17, 325, (1964).

1.6 $Os(phen)_3Cl_2$ $Os(phen)_3Cl_2$ was prepared as for $Os(bipy)_3Cl_2$ (see section 1.5 above).

1.7 $Cr(bipy)_3ClO_4)_3$ $Cr(bipy)_3ClO_4)_3$ was prepares as follows:

A solution of electrolytic chromium (0.52 g, 0.01 mol) in concentrated hydrochloric acid (5 ml) and water (5 ml) was prepared in an ultrasound bath. After all the metal was dissolved and $H_2$ evolution ceased, the solution was diluted with water (40 ml). 2,2'-bipyridine (4.7 g) dissolved in some aethanol was added immediately giving a deep wine-red solution which was filtered. The filtrate was then treated with a solution of sodium perchlorate (2.00 g ) and 70% perchloric acid (1 ml) in water (200 ml). This precipitated black crystals which were collected by filtration. These crystals, which were taken to be tris (2,2'-bipyridine) chromium (II) perchlorate, were converted to the yellow chromium (III) species by stirring with 1M perchloric acid with oxygen bubbled through the solution overnight. The yellow precipitate was filtered off and recrystallized from warm water to give yellow needle-like crystals (1.73 g).

The reaction was carried out under $N_2$ atmosphere.

1.8 $Cr(phen)_3(ClO_4)_3$ $Cr(phen)_3(ClO_4)_3$ was prepared as follows:

All solutions were degassed before use by sonication and nitrogen bubbling. 0.52 g of chromium (3DE) was dissolved in 2.5 ml of concentratd hydrochloric acid and 2.5 ml of water under nitrogen. The solution was sonicated for 3 hours to dissolve all the chromium. After the chromium had dissolved, 40 ml of water was added with stirring. The solution changed colour from pale blue/green to black and then 2.0 g of sodium perchlorate was added in 5 ml of water. This gave a dark green precipitate immediately which was filtered under nitrogen. This compound was $Cr(phen)_3^{2+} 2ClO_4^-$. The solid was quickly transferred to a flask containing 1 M perchloric acid and oxygen was bubbled through it for 3 hours. (Nitrogen is no longer required).

The dark green precipitate turned to a yellow solid which was collected by filtration. This material was crude and was purified by washing the precipitate with water. The $Cr(phen)_3^{2+}3ClO_4^-$ was found as a fine yellow precipitate in the filtrate while the impurity (pale pink) was left in the funnel.

The compounds prepared in Sections 1.1 to 1.8 above were tested for their fluorescence properties, and the results are shown in Table 1. The results indicated that all the complexes have half-lives of emission which are acceptable for a time-resolved luminscence binding assay. The ruthenium and iridium complexes have however surprisingly long half-lives making them especially suitable for the application. Iridium complexes in particular exhibit maximum excitation wavelengths which render such complexes especially suitable for laser excitation using readily available and cheap types of laser.

The complexes each provide useful starting materials for the preparation of derivatised complexes adapted for conjugation with binding partners such as antigenic compounds, antibodies or antibody fragments.

In Table 1, the maximum excitation wavelength ($\lambda$ex) was measured using a $10^{-4}$M solution of the complex in phosphate buffered saline (PBS) scanned from 250 to 600 nm for ruthenium, 250 to 500 nm for iridium, 360 to 500 nm for chromium and 300 to 600 to nm for osmium, against a buffer blank on a Perkin-Elmer $\lambda$5 spectrophotometer. The maximum emission wavelength ($\lambda$ em) was measured using a suitably diluted solution of the complex is PBS and scanning the fluorescence emission from 500 to 700 nm (ex. 450 nm) for ruthenium, 450 to 550 nm (ex 366 nm) for iridium,

TABLE I

|  |  | Ru | Ir | Cr | Os |
|---|---|---|---|---|---|
| (bipy)$_3$ | $\lambda$ex | 475 nm | 310 | 420 | 480 |
|  | $\lambda$em | 610 nm | 495 | 728 | 730 |
|  | Q | — | 0.09 | $10^{-4}$ | — |
|  | $\tau(H_2O)$ | 460 nsec | 327 | 150 | 130 |
| (phen)$_3$ | $\lambda$ex | 470 nm | 350 | 420 | 480 |
|  | $\lambda$em | 610 nm | 498 | 728 | 730 |
|  | Q | — | — | — | — |
|  | $\tau(H_2O)$ | 560 nsec | 720 | 170 | 130 |

Key:
$\lambda$ex = maximum excitation wavelength
$\lambda$em = maximum emission wavelength
Q = quantum yield (aereated solution unless otherwise stated)
$\tau(H_2O)$ = lifetime of fluoroescence decay 700 to 750 nm (ex 420 nm) for chromium and 650 to 800 nm (ex 480 nm) for osmium. The quantum yield (Q) was calculated against a standard of known yield using the following relationship:

$$\frac{Q_x}{Q_s} = \frac{I_x}{I_s} \times \frac{A_s}{A_x}$$

where I=fluorescence intensity, A=absorbance and Q=Quantum yield. Quinine sulphate was used as a standard for iridium complexes and Rhodamine B for ruthenium complexes. The fluorescence life-times (($\tau H_2O$) of the complexes was calculated from the fluorescence decay profile obtained after laser flash excitation or by time correlated single photon counting on a nano second life-time fluorimeter.

A further series of iridium and ruthenium complexes were prepared as follows:

1.9 $Ir(bipy)_2(4'-[4-(1,10-phenanthroline)]-phenoxy-acetic acid)^{3+}(Ir(bipy)_2IV^{3+})$ $Ir(bipy)_2IV^{3+}$ was prepared by first preparing $Ir(bipy)_2$ as described in Inorg. Chem. 10, (9). 1971, 2002–2009 and then adding ligand IV. Ligand IV was prepared as follows:

A solution of 4-(4'-hydroxyphenyl)-1,10-phenanthroline (0.84 g, 3.272×$10^{-3}$ mol) in hexamethylphosphoramide (HMPA) (20 ml) was added to a suspension of potassium tert-butoxide (0.55 g, 4.91×$10^{-3}$ mol ) in HMPA (20 ml) and the mixture stirred for 0.5 h at 20° C. ($N_2$ atm.). Lithium $\alpha$-bromacetate (0.47 g) was added and the mixture stirred at 20° C. for 72 h. Water (150 ml) was added. The pH was adjusted to 4.5 with 2.5 M HCl(aq) and the mixture extracted with n-butanol (3×70 ml). The n-butanol extracts were dried ($Na_2SO_4$), concentrated to 40 ml in vacuo, and treated with diethyl ether (150 ml). The buff precipitate was filtered, washed with ether and dried in vacuo to give 4'-[(1,10-phenanthroline)]-phenoxy acetic acid (0.39 g).

ligand IV was added as described in J. Inorg. Nucl. Chem. 41, 495–507 (1979) and generally as described in Section 1.3 above.

1.10 $Ir(bipy)2-(4''-carboxybenzyl-4'-[4-(1,10-phenanthroline)]phenyl ether^{3+}(Ir(bipy)_2III^{3+}$ $Ir(bipy)_2^{3+}$ was prepared by first preparing $Ir(bipy)_2III^{3+}$ (see Section 1.3 above) and then adding ligand III. Ligand III was prepared via 4-(p-methoxyphenyl)-1,10-phenanthroline (Ligand I) and 4-(p-hydroxyphenyl)-1,10-phenanthroline (Ligand II), as follows:

A suspension of 8-aminquinoline (7.22 g, 0.05 mol) in 75% arsenic acid (9.5 ml, 0.10 mol) and 85% orthophosphoric acid (50 ml) was stirred at 100° C. until dissolution occurred and the solution treated at 100° C. with p-methoxy-$\beta$-chloropropiophenone (12.8 g, 0.07 mol) at such a rate as to maintain the temperature at 120° C. (1 hour). The temperature was raised to 135°–140° C. and kept at 140° C. for 1½ hours. The mixture was poured on to ice (400 ml) and the aqueous solution made alkaline (to pH 8.5) with 30% potassium hydroxide. The brown tarry precipitate was filtered through Celite and extracted into hot benzene/toluene (4×200 ml) and $CHCl_3$ (20 ml). The extracts were concentrated to a brown tar which was treated with toluene (300 ml) and extracted with 2.0M HCl(aq) (3×250 ml) (El). The 2.0M HCl(aq) extracts slowly yielded prisms on cooling. A sparingly water soluble buff precipitate and brown viscous tar formed between the solvent layers. This precipitate was extracted into hot 2.0M HCl(aq) 2×300 ml) E2). The extract E1 and E2 were concentrated in vacuo and the residues treated with water (100 ml). The suspensions were neutralised with 30% potassium hydroxide (aq) and extracted into $CHCl_3$. E2 yielded a pale brown oil (4.51 g)-t.l.c. (neutral alumina, $CHCl_3$), one major (fluorescent)

component RF 0.7 and brown baseline components. The oil was subjected to dry column flash chromatography (basic alumina, CHCl$_3$) to give and off white oily solid (3.88 g, 27%).

E1 yielded a yellow semi-solid (3.0 g) which proved difficult to purify further from minor impurities, but contained the desired product 4-(p-methoxyphenyl)-1,10-phenanthroline (Ligand I) as the predominant component.

A stirred suspension of sodium hydride (50% dispersion, 5.76 g, 0.0127 mol) in dimethyl formamide (10 ml) was treated dropwise with a solution of ethanethiol (0.81 ml, 0.0115 mol) in dimethyl formamide (10 ml) at 20° C. (N$_2$ atm) and the mixture stirred at 20° C. for 0.5 hours. 4-(p-methoxyphenyl)-1,10-phenanthroline (0.55 g, 1.92× 10$^{-3}$ mol) was added and the mixture heated under reflux for 3 hours. Water (150 ml) was added and the yellow solution extracted with toluene (4×100 ml) and CHCl$_3$ (100 ml). The pH of the aqueous layer was adjusted from 12.5 to 7.5 with 2.0M HCl(aq) and the aqueous layer extracted were dried (MgSO$_4$) and concentrated in vacuo to a buff solid 4-(p-hydroxyphenyl)-1,10-phenanthroline (Ligand II) (0.28 g, 54%) T.L.C. (neutral alumina; 2-BuOH—H$_2$O-Acetic acid, 13:6:2)—gives a very pale yellow spot RF 0.65).

A solution of 4-(p-hyroxyphenyl)-1,10-phenanthroline (0.51 g in hexamethylphosphoramide (HMPA) (20 ml) was treated with potassium t-butoxiede (0.32 g, 2.82×10$^{-3}$ mol) at 20° C. (N$_2$ atm) and stirred at 20° C. for 0.5 hours. The yellow solution was treated with lithium α-bromo-p-toluate (0.42 g, 1.90×10$^{-3}$ mol) and the mixture stirred at 20° C. for 24 hours. Water (50 ml) was added and the pH adjusted to 4.5 with 2.0M BCl(aq). The mixture was concentrated in vacuo to 20 ml and dimethyl ether (120 ml) added. The buff precipitate was filtered through cellulose and washed with dimethyl ether (100 ml). The cellulose and residue were extracted with DMF (3×30 ml) and the extracts concentrated to a buff solid.

T.L.C. on silica gel (2-BuOH—H$_2$O-acetic acid, 13:6:2 revealed a major fluorescent component RF 0.57, a minor component RF 0.86 and brown baseline products.

The crude solid was purified by dry column flash chromatography (silica gel, CHCl$_3$—MeOH (1:1)) to give a pale buff solid 4"-carboxybenzyl-4"-[4-(1,10-phenanthroline)] phenyl ether Ligand III) (0.52 g, 75%). T.L.C.-one spot (fluorescent) (silica gel, CHCl$_3$—MeOH (1:1)-1% acetic acid), RF 0.62.

Ligand III was added to Ir(bipy)$_2$ substantially as described in J. Inorg. Nucl. Chem., 41, 495–507, (1979) and generally as described in Section 1.3 above.

1.11 Ir(bipy)$_2$ (4,7-diphenyl-1,10-phenanthroline)$^{3+}$ (Ir (bipy)$_2$ DPPhen$^{3+}$)

Ir(bipy)$_2$ DPPhen$^{3+}$ was prepared by first preparing Ir(bipy)$_2$$^{3+}$ (see Section 1.3 above) and then adding DPPhen as described in J. Inorg. Nucl. Chem., 41, 495–507, (1979) an generally as described in Section 1.3 above.

1.12 Ir(bipy)$_2$ (2,2'-biquinoline)$^{3+}$ (Ir(bipy)$_2$Biquin$^{3+}$ (Ir(bipy)$_2$Biquin$^{3+}$ was prepared by first preparing Ir(bipy)$_2$$^{3+}$ (see Section 1.3 above) and then adding Biquin substantially as described in J. Inorg. Nucl. Chem., 41, 495–507, (1979) and generally as described in Section 1.3 above.

1.13 Ir(phen)$_2$(4'-[4(1,10-phenanthroline)]-phenyoxyacetic acid$^{3+}$ (Ir(Phen)$_2$IV$^{3+}$)

Ir)phen)$_2$IV$^{3+}$ was prepared by first preparing Ir(Phen)$_2$$^{3+}$ (see Section 1.4 above) and then adding Ligand IV (see Section 1.9 above) substantially as described in J. Inorg. Nucl. Chem., 41, 495–507, (1979) and generally as described in Section 1.3 above.

1.14 Ru(bipy)$_2$(4-(3-hydroxypropyl)-4'-methyl-2,2'-bipyridine)$^{2+}$ (Ru(bipy)$_2$(bipyMe((CH$_2$)$_3$OH))$^{2+}$)

(Ru(bipy)$_2$(bipyMe((CH$_2$)$_3$OH))$^{2+}$ was prepared by first preparing Ru(bipy)$_2$$^{3+}$ (see Section 1.1 above) and then adding bipy Me((CH$_2$)$_3$OH). Bipy Me((CH$_2$)$_3$OH) was prepared as follows:

N-butyl lithium (18 ml of 1.57M) was added to a solution of diisopropylamine (4 ml) in dry THF (15 ml) and the resulting mixture was left stirring for 15 minutes. 4,4'-dimethyl-2,2'-bipyridine (5 g, 0.03 mol) in dry THF (125 ml) was then added slowly. After 2 hours a saturated solution of ethylene oxide (1.26 g, 0.03 moles in 10 ml THF) was added at approximately 0° C. and stirring continued for 30 minutes in the cold and 15 minutes gently refluxing. After this time, the reaction mixture had turned red and water was added to the solution, which was then extracted with ether. The ether was dried with anhydrous Na$_2$SO$_4$, filtered and removed under vacuo to give a brown oil containing a white solid (starting material). This oil was then triturated with a small amount of ethanol, precipitating out the white solid. This was filtered and the ethanol removed under reduced pressure, to give a brown semi-solid oil.

1.15 Ru(phen)$_2$(4"-carboxybenzyl-4'-[4-(1,10-phenanthroline)]phenylether$^{2+}$ (Ru(phen)$_2$III$^{2+}$)

Ru(phen)$_2$III$^{2+}$ was prepared by first preparing Ru(phen)$_2$$^{2+}$ (see Section 1.2 above), then adding Ligand II as follows:

A solution of Ru(phen)$_2$Cl$_2$ (0.65 g, 1.508×10$^{-3}$ mol) in boiling ethanol-water (1:1) (40 ml) was treated with 4-(4'-hydroxyphenyl)-1,10-phenanthroline (0.45 g, 1.508×10$^{-3}$ mol) in hot ethanol (40 mol) and the mixture heated under reflux (N$_2$ atm) for 3 h. Concentration in vacuo yielded a solid which was chromatographed on Sephadex LH20 EtOH) to give the desired complex as an orange solid (1.1 g 100%).

Ru(phen)$_2$II$^{2+}$ was then converted to Ru(phen)$_2$III$^{2+}$ as follows:

A suspension of sodium hydride (0.078 g, 1.615×10$^{-3}$ mol) in dimethylformamide (5 ml) was slowly treated with a solution of Ru(phen)$_2$ [4-(4'-hydroxyphenyl)-1,10-phenanthroline]Cl$_2$ (0.13 g, 3.23×10$^{-4}$ mol) in dimethylformamide (10 ml) at 20° C. (N$_2$ atm) and mixture stirred at 20° C. for 5 h. α-Bromo-p-toluic acid (0.069 g, 3.23×10$^{-4}$ mol) was added and the mixture stirred at 20° C. for 48 h. Water (100 ml) was added, the pH adjusted to 1.5 with 2.0M hydrochloric acid and the solvent removed in vacuo. The brown residue was chromatographed on cellulose (2-butanol-water-acetic acid, 8:1:1) to give the desired complex as a yellow solid (0.07 g, 46%).

1.17 Ru(phen)$_2$(4'-[4-(4-(1,10-phenanthroline)]-phenoxyacetic acid (Ru(phen)$_2$IV$^{2+}$)

Ru(phen)$_2$IV$^{2+}$ was prepared by first preparing Ru(phen)$_2$$^{2+}$, then adding ligand II as described in Section 1.16 above. Ru(phen)$_2$II$^{2+}$ was then converted to Ru(Phen)$_2$IV$^{2+}$ as follows:

A suspension of sodium hydride (0.18 g, 3.42×10$^{-3}$ mol) in dimethylformamide (DMF) (20 ml) was slowly treated with a solution of Ru(phen)$_2$ [4-(4'-hydroxyphenyl)-1,10-phenanthroline]Cl$_2$ (0.43 g 5.34×10$^{-4}$ mol) in DMF (25 ml) at 20° C. (N$_2$ atm) and the mixture stirred at 20° C. for 0.5 h. α-Bromoacetic acid (0.13 g, 9.18×10$^{-4}$ mol) and additional sodium hydride was added and the mixture heated at 140° C. for 18 h. Water (100 ml) was added, the pH adjusted 3.0 with 2.5 M hydrochloric acid and the solvent removed in vacuo. The ethanol extracts were concentrated in vacuo and the brown residue chromatographed on Sephadex LH20 (EtOH eluent) and cellulose (2-butanol-water-acetic acid, 13:6:2) to give the desired complex as a yellow solid (0.12 g, 26.5%).

(Treatment of Ru(phen)$_2$Cl$_2$ in ethanol-water (1:1) with 4'-[4-(1,10-phenanthroline)]-phenoxyacetic acid in ethanol as described above also yielded the desired complex).

1.18 Ru(phen)$_2$ (4,7 diphenylphenanthroline disulphonic acid)$^{2+}$ (Ru(phen)$_2$dpphen(OSO$_3$H)$_2$$^{2+}$ 0.20 g Ru(phen)$_2$Cl$_2$ 2H$_2$O (mw 568) was added to 0.30 g bathophenanthroline disulphonic acid disodium salt, hydrate (mw 536.5, Aldrich) and these were dissolved in 30 mls of water and 5 mls of methanol. The mixture was heated at reflux temperature for 2 hours producing a red suspension. The mixture was cooled and the red precipitate filtered and washed with ether (4×40 ml). The solid was then recrystalised from water and dried overnight under vacuum over P$_2$O$_5$. (Yield 0.20 g.)

1.19 Ru(phen)$_2$ (4,7 diphenylphenanthroline disulphonyl chloride)$^{2+}$ (Ru(phen)$_2$dpphen(OSO$_2$Cl)$_2$$^{2+}$ 0.05 g Ru(phen)$_2$dpphen(OSO$_3$H)$_2$$^{2+}$2Cl$^-$ 3H$_2$O (see Section 1.18) was carefully dissolved in 10 ml of chlorosulphonic acid. This was heated to 120° C. for 2 hours under nitrogen. The colour changed from red to green corresponding to oxidation of Ru II to Ru III. The mixture was cooled to 0° C. and then was carefully added, dropwise, to about 300 mls of ice. A red solution formed immmediately and this was extracted with dichloromethane 12×150 ml). The extract was dried for 2 days with calcium chloride. The drying agent was removed and the extract reduced to a solid by rotary evaporation. A red solid was produced in varying yields (reaction repeated several times) and dried over P$_2$O$_5$ under vacuum. (Yield 1–15 mg).

Fluorescence measurements showed the compound to be a typical Ru tris-phenanthroline compound but the short lifetime (see Table II) indicated a convalently bound halogen (Cl) was present which when lost, on conjugation to antibody gave a long lifetime similar to the parent sulphonic acid.

The fluorescence characteristics of the complexes described in Section 1.9 to 1.19 inclusive were measured and are shown in Table II.

TABLE II

| | | λex nm | λem nm | Q | τ nsec |
|---|---|---|---|---|---|
| Iridium (bipy)$_2$IV$^{3+}$ | 1.9 | 310 | 495 | 0.08 | 377 |
| Iridium (bipy)$_2$III$^{3+}$ | 1.10 | 310 | 495 | 0.09 | 1850 |
| Iridium (bipy)$_2$ DPPhen$^{3+}$ | 1.11 | 308 | 495 | 0.04 | 310 |
| Iridium (bipy)$_2$ Biquin$^{3+}$ | 1.12 | 310 | 495 | 0.03 | 505 |
| Iridium (phen)$_2$IV$^{3+}$ | 1.13 | 337 | 508 | — | 718 |
| Ruthenium(bipy)$_2$ bipyMe:(CH$_2$)$_3$OH | 1.14 | 450 | 625 | 0.02 | 269 |
| Ruthenium(bipy)$_2$III$^{2+}$ | 1.15 | 450 | 630 | — | 410 |
| Ruthenium(phen)$_2$III$^{2+}$ | 1.16 | 420 | 650 | — | 1140 |
| Ruthenium(phen)$_2$IV$^{2+}$ | 1.17 | 420 | 650 | — | 1125 |
| Ruthenium(phen)$_2$ phen(phenyl SO$_2$Cl)$_2$$^{2+}$ | 1.18 | 440 | 625 | 0.015 | 265 |
| Ruthenium(phen)$_2$ phen(phenyl SO$_3$H)$_2$$^{2+}$ | 1.19 | 440 | 625 | — | 788 |

2. Preparation of Complex/Antibody Conjugates

The complexes described in Section 1.1 to 1.19 above may be covalently attached to antibody be derivatising (or activating) one of the ligands. Suitable such derivatives include active esters, such as N-hydroxysuccinimide ester (NHS) and other reactive groups such as chloroformates and isothiocyantes.

2.1 General Conjugation Method

Pure conjugates of antibody metal chelate, free of unreacted chelate were produced using N-hyroxysuccinimide esters, chloroformates or isothiocyanates of transition metal chelates, and antibody.

Materials and Methods
Dimethyl formamide (DMF)
0.05M carbonate-bicarbonate buffer pH 9.6
Sephadex G-25
Phosphate buffered saline (PBS)
Conjugation A 200, 100 or 50 molar excess of the chelate in solution in DMF was added dropwise to a solution of antibody in 0.05M carbonate/bicarbonate pH 9.6 at a 5:1 volume excess of antibody to activated chelate. The reaction was left overnight at room temperature, with gentle agitation in the dark.

Reaction conditions

| Ab:chelate | |
|---|---|
| 1:50/100/200 | M:M |
| 50:1 | vol/vol |

Separation

After reaction, the mixtures were centrifuged for 3 min. at 12,000×g and any pellet formed discarded. The supernatant was fractionated on a Sephadex G-25 column (1×30 cm) on PBS at 0.5 ml min. 1 ml fractions were collected. The O.D. of the eluted fractions were read at 280 nm and at the λex max for the respective chelates. The fractions containing the protein were pooled and concentrated using Amicon CM30 concentrators.

Results

Two peaks were eluted from the column, the smaller leading peak corresponded to the protein fraction and the large second peak unconjugated chelate. Any absorbance at the chelate λex max present in the protein fraction was taken to indicated covalent attachment of the metal chelate to the antibody and this was confirmed by gel electrophoresis on a Beckman SPE-II system.

2.2 Ru(bipy)$_2$III)Cl$_2$/Antibody Conjugate

Ru(bipy)$_2$(III)Cl$_2$ (0.24 g, 2.82×10$^{-4}$ mol) in dry acetonitrile (30 ml) was heated with disuccinimidal carbonate (0.36 g, 1.41×10$^{-3}$ mol) and the mixture stirred at 50° C. (N$_2$ atm) for 24 hours. The mixture concentrated in vacuo and the orange residue chromatographed on Sephadex LH20 (methanol eluent) to give an orange solid (0.2 g). T.L.C. (cellulose; CHCl$_3$—MeOH (1:1) gave one spot RF 0.9. The product was conjugated to an anti-thyroid stimulating hormone (TSH) monoclonal antibody by the general method described in Section 2.1 above.

2.3 Ir(bipy)$_2$ 4-phenyl-7-phenyl(4'-phenyl acetic acid), 1,10 phenanthroline$^{3+}$/Antibody Conjugate (Ir(bipy)$_2$V$^{3+}$/Antibody conjugate)

Ir(bipy)$_2$V$^{3+}$ was prepared as follows:

To a stirred solution of Ir(bipy)$_2$dpphen$^{3+}$ (50 mg in chloroform (10 ml) was added potassium acetate (8.6 mg) and 4-diazo-phenylacetic acid (27 mg) and the mixture stirred at R.T. for one hour. Evaporation in vacuo gave a residue which was dissolved in MeOH and chromatographed on LH-20, eluting with methanol. The greenish luminescent band was collected and isporopanol (20 ml) added to it. Evaporation in vacuo gave a yellow solid. (Yield: 30 mg).

The complex was activated to the N-hydroxysuccinimide ester and conjugated to an anti-TSH monoclonal antibody as described in Section 2.2 above 2.4 Ru(bipy)$_2$bipy(CONCS)$_2$$^{2+}$/Antibody Conjugate The 2,2' bipyridine 4,4' diacylisothiocyante ligand was prepared via a diacyl chloride derivative.

1.0 g of 2,2' bipyridine 4,4' dicarboxylic acid was suspended in 200 ml of dry toluene and 25 ml of thioyl chloride. This mixture was heated at reflux temperature, under nitrogen until all the solid dissolved and a pink/orange solution persisted. The thionyl chloride was fractionally distilled from the solution and more toluene was added (100 ml). The fractional distillation was repeated until about 50 ml of solution was left. This was reduced to a solid by rotary evaporation leaving a cream/yellow solid. This was dried by pumping down for 4 hours. (Yield: 0.5 g)

Analysis: Infrared—characteristic acyl chloride peak at 1780 $cm^{-1}$.

0.20 g of 2,2' bipyridine 4,4' diacyl chloride was added to 0.42 g of potassium thiocyante in 800 ml of dry acetone. The solution as heated and stirred for one hour after which it was filtered while still hot. The solution was allowed to cool and the solvent removed by rotary evaopration giving a yellow solid that was very soluble in acetone (starting material is only sparingly soluble in acetone). (Yield: 0.31 g).

Analysis: Infrared shows characteristic aromatic and isothiocyanate stretches at 1630 $cm^{-1}$ (arom C—C) and 2064 $cm^{-1}$ (N=C=S).

0.25 g of $Ru(bipy)_2Cl^2 \cdot 2H_2O$ added to 0.31 g of 2,2'bipyridine 4,4'diacylisothiocyanate. These were dissolved in 50 ml of HPLC grade acetonitrile (Rathburn) and heated at reflux tremperature for 2 days under nitrogen. The solvent was then removed by rotary evaporation until about 3 ml remained. 200 ml of water was added with swirling. The unreacted $Ru(bipy)_2Cl_2 \cdot H_2O$ and $bipy(CONCS)_2$ precipitated. These were quickly removed leaving a red solution. (This part of the work involving aqueous solutions must be done quickly so as to minimise hydrolysis of any isothiocyante groups on the complex). To the red solution an excess (0.5 g) of ammonium hexafluorphosphate was added and it produced a red precipitate instantaneously. The precipitate was recovered by filtration and dried over silica under vacuum for 24 hrs. (Yield: 0.15 g).

Analysis: Infrared shows characteristic —N=C=S peak at 2101 $cm^{-1}$ range in literature 2150–205 $cm^{-1}$ (—S—C—N isomer is not seen—2170–2135 $cm^{-1}$ also $CH_3CN$ not seen—2260–2240 $cm^{-1}$).

2.5 $Ru(bipy)_2bipy(Me)(CH_2)_3OH$/Antibody Conjugate cis-dichlorobis (2,2'-bipyridine ruthenium (II)) (484 mg, 1 mmol) and 4-(3-hydroxyprophyl)-4'-methyl-2,2'-bipyridine (0.2739 g, $1.2 \times 10^{-3}$ mol, (a slight excess is used to allow for impurities present) were heated to reflux in ethanol (250 ml) for 19 hours under nitrogen. After 19 hours TLC showed a predominant orange spot at the baseline (product) and a very faint fast reaction mixtrue was then filtered hot and treated with a solution of ammonium hexafluorophosphate (1.00 g) in methanol (20 $cm^3$) and allowed to cool. On cooling red crystals precipitated out slowly, which were collected by filtration.

Bis(2,2'-bipyridine)(4-[3-hydroxypropyl]-4'-methyl-2,2'-bipyridine) ruthenium (II) hexafluorophosphate (0.1151 g, $1.15 \times 10^{-4}$ mol) was dissolved in the smallest possible volume of dry THF. This was then added dropwise to 12.5% w/w phosgene in toluene (5 ml). After addition, the solution was stirred for a further half hour and then unreacted phosgene was removed using a water pump. The reaction mixture was then evaporated to dryness to leave a small amount of orange coloured solid.

Electronic spectra: Excitation max. 480 nm

Emission max. 610 nm.

IgG (2.82 mg, $1.88 \times 10^{-8}$ mol) was dissolved in labelling buffer (pH 9.4)(1 ml). The complex (2.00 mg, $1.88 \times 10^{-6}$ moles) in 100 molar excess DMP (1/10 ml) was added slowly to the IgG solution, to avoid denaturing the protein by the heat produced. The resulting solution was then left in the fridge overnight.

A column (Sephadex G-25) was run of the labelling solution eluting with PBS buffer (pH 7.4). The column showed a birghtly coloured band which was collected. The fraction was shown to contain antibody.

Electronic spectra: Excitation max 469 nm

Emission max. 610 nm.

2.6 $Ru(phen)_2dpphen(SOCl_2)_2^{2+}$/Antibody Conjugate $Ru(phen)_2ddpphen(SO_2CL_2)_2^{2+}$ (see Section 1.18) was conjugated to a human gamma globulin.

The flourescence characteristics of the conjugates described in Section 2.1 to 2.6 inclusive are given in Table III.

TABLE III

| Activated Chelates | λex nm | λem nm | τ nsec |
|---|---|---|---|
| Iridium(bipy)$_2$dp-phen$^{3+}$ (phenyl acetate)-N-hydroxsuccinimide ester (V) | 366 | 500 | 152 |
| Ruthenium(bipy)$_2$III$^{2+}$-N-hydroxysuccinimide ester | 450 | 630 | 410 |
| Ruthenium(bipy)$_2$bipy(me); (CH$_2$)$_3$OH (chloroformate deriv.)$^{2+}$ | 469 | 610 | 476 |
| Ruthenium(bipy)$_2$bipy(CONCS)$_2$$^{2+}$ | 470 | 620 | 125 |
| Ruthenium(phen)$_2$dp-phen(SO$_2$Vl)$_2$$^{2+}$ | 470 | 620 | 1200 |

2.2 and 2.3 conjugated to anti-TSH MAb 2.4 to 2.6 conjugated to human-gamma globulin 3. Preparation of Complex/Antibody Conjugates A synthesis was performed to prepare ruthenium (II) tris bipyridyl derivatives and to bind the derivatives to a monoclonal antibody. Isothiocyanate and active ester derivatives of bipyridyl were prepared to provide functional groups on the bipyridyl molecule, for covalent attachment to amino groups on the antibody.

The synthesis is shown diagramatically in Scheme 1.

The synthesis steps were conducted as follows:

Step (a) Synthesis of 4,4'dimethyl 2,2'bipyridine. Freshly distilled 4-picoline (600 ml) was refluxed with palladium on carbon 10% (w/v) for five days. The mixture was then refluxed for a further hour after addition of 100 ml of hot benzene. The palladium on carbon was then removed by filtration (glass-fibre paper). The filtration was repeated until a clear yellow solution was obtained. The volume of the solution was reduced by rotary evaporation of about 200 ml. and was left to stand for 24 hours. White crystals appeared which, after collection, were recrystalised from ethyl acetate. A colourless solid was recovered.

Yield; 17 g.

Step (b) Preparation of 4,4'-dicarboxy-2,2'-bipyridyl. 400 ml of water was added to 4 g of 4,4'dimethyl 2,2'bipyridyl and 25 g of potassium permanganate. This mixture was refluxed for 14 hours. Brown manganese dioxide was precipitated and was removed filtration after the reflux. The filtrate was washed with ether three times, (to remove unreacted starting material) and the aqueous phase was retained. Concentrated hydrochloric acid was then added dropwise to the

SCHEME 1

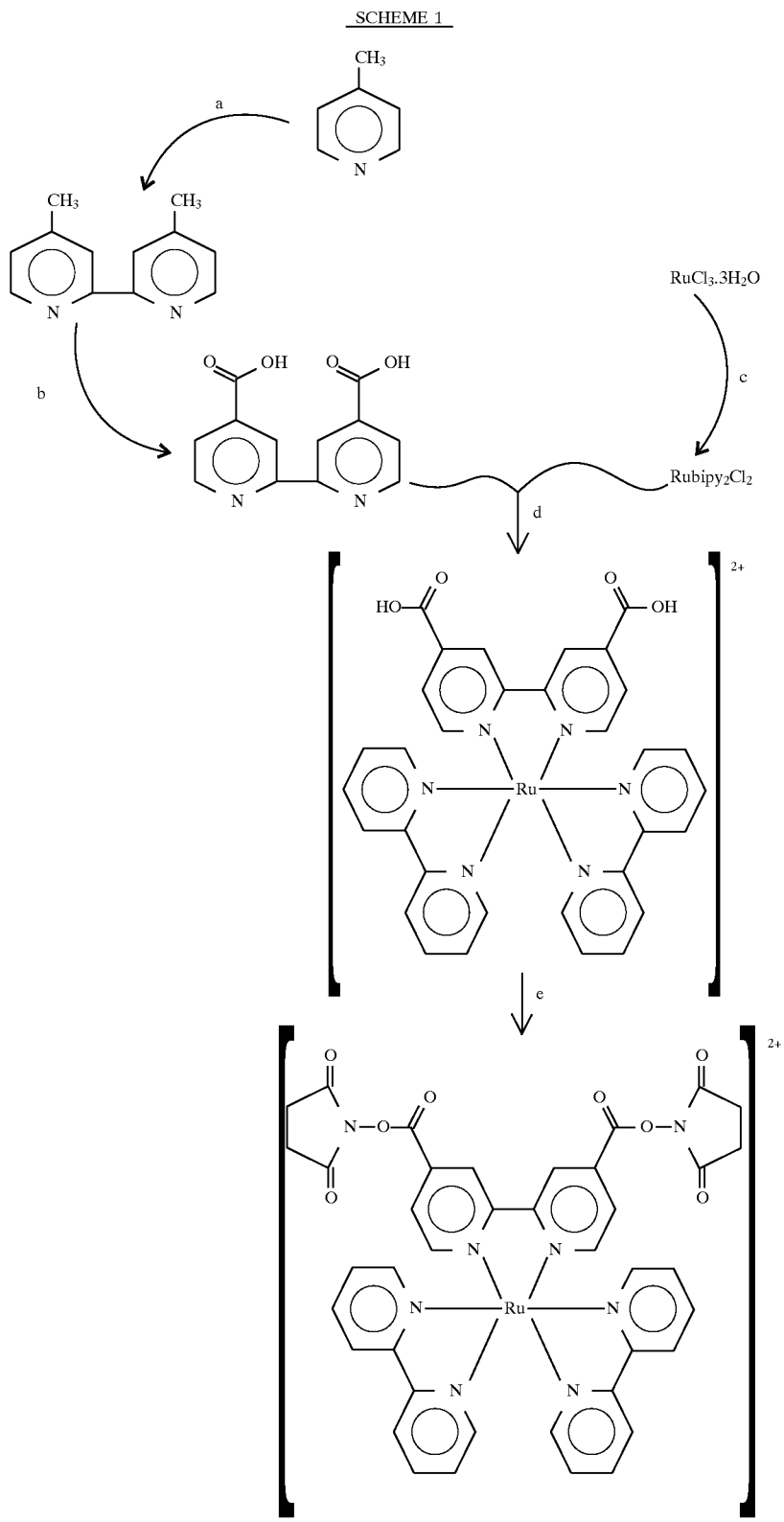

aqueous phase, with stirring, until a fine white precipitate persisted. This precipitate was collected by filtration and ried over silica under vacuum for 24 hours.

Yield: 1.7 g (24%)

Step (c) Preparation of ruthenium bis bipyridyl dichloride. Ru(bipy)$_2$ Cl$_2$.2H$_2$O. A mixture of ruthenium trichloride trihydrate (2.5 g), 2,2' bipyridyl (3.0 g) and lithium chloride (5.0 g) was placed in 50 ml of DMF under nitrogen. This mixture was stirred and refluxed for 7 hours. The resulting purple/black solution was allowed to cool slowly to about 15° C. with continued stirring. 250 ml of acetone was then added and the flask stoppered under nigrogen. This solution was left at 0° C. for 24 hours. A black microcrystalline solid was recovered by filtration which was washed with water three times and diethyl ether three times.

Yield: 3.0 g

Step (d) Preparation of ruthenium tris bipyridyl dicarboxylic acid [Ru(bipy)$_2$bipy(CO$_2$H)$_2$]$^{2+}$ Ruthenium bis bipyridyl dichloride (520 mg), 4,4' dicarboxy 2,2' bipyridyl (300 mg) and sodium bicarbonate (330 mg) were placed in 15 ml of waer and 10 ml of methanol. This mixture was refluxed for 2 hours with stirring. The colour of the solution changed from black/purple to a bright red solution. The solution was cooled and 25 ml of saturated aqueous ammonium hexafluorophosphate was added. The resultant solution was left at 0° C. for 18 hours and orange-red crystals were recovered by leaving the solution open to the atmosphere for a few hours at room temperature and collecting the crystals by filtration.

Yield: 0.2 g

Fluorescence excitation 288 nm 456 nm 466 nm 466 nm emission 638 nm broad

Step (e) Preparation of ruthenium tris bipyridyl N-hydroxysuccinimide derivative. 38 mg of ruthenium bipyridyl diacid, 18 mg of N-hydroxysuccinimide, and 32 mg of dicyclohexylcarbodiimide (DCCI) (excess) were stirred together at room temperature in DMF for 2 hours. The DCCI reacts to become DCU. The solution in DMF of the active ester (0.1 ml) is then added to antibody. (1 ml aqueous base containing antibody).

Analysis by fluorescence:
  emission 647 nm,
  solvent DMF,
  exitation 475 nm

The compound prepared in step (e) above was added to antibody to form conjugates.

A known weight of antibody was plced in 1 ml of labelling solution in aqueous base, for example, Na$_2$CO$_3$ at 0.1M. To this known weight of antibody was added a ten-fold excess of label in 0.1 ml DMF. The DMF solution was added very slowly to avoid damge to the antibody. The labelled solution was then left at 0° C. for 18 hours to allow conjugation to occur.

The separation of the unreacted label was performed using one of three method:

1. Passing the labelled solution through a PIO column (Sephadex) eluting with a phosphate suffer solution (PBS).
2. Dialysing the labelled solution in PBS and then pass the solution through the PIO column as above.
3. Passing the labelled solution through a G25 Sephadex column (in a 10 ml pipette) eluting with PBS. Methods 2 and 3 proved satisfactory for the separation of these solutions. Method 1 involves a little uncertainty in separating the fractions as the column was of insufficient length. The separation methods above were tried with a solution of antibody and Ru(bipy)$_2$bipy(CO$_2$H)$^{2+}$ and should remove the ruthenium complex completely from the antibody. This was achieved with methods 2 and 3.

Table of Results

| Type of IgG | Type of Label | Method of Sepn. | Does it Work? |
|---|---|---|---|
| Goat anti-Mouse | NHS | 2 | Yes |
| Anti TSH | NHS | 2 | Yes |
| Human | NHS | 3 | Yes |

The answer "yes" indicates that some ruthenium tris bipyridyl derivative was retained in the antibody fraction after separation. This was often seen by the naked eye and always checked by fluorescence spectroscopy.

The metal-labelled antibody may be used in existing equipment for performing a time-resolved luminescence immunoassay.

The complexes that have been convalently linked to an antibody may be tested by dissolving the complex-antibody conjugate in aqueous, aerated base of pH about 7.5. This solution should have an optical density of 1 with respect to the excitation wavelength of the complex. Then, using a laser or spark source, the lifetime of the luminescent emission may be recorded.

4. Assay Method 4.1 General Method

A two-site immunoassay may be performed in a microtitre plate format. It utilises two monoclonal antibodies which bind to separate epitopes on the analyte molecule.

The concentration of analyte is quantified by incubation with an anti-analyte monoclonal antibody immobilised in micro titre plate wells. A fluorescent-labelled second antibody is then added to the antibody-antigen complex in the wells. After the second incubation step, unreacted label is washed off and the immobilised antibody-antigen-antibody fluorophor complex is eluted off the plates in an acid solution, prior to measurement of fluorescence.

Fluorescence was measured by the method of Phase-Resolved fluorescence spectroscopy. "Phase-Resolved fluoroimmunoassay of Human Serum Albumin" Tahout, Y. R., McGowen, L. B. (1986), Analytical Chemistry Acta Vol. 182, 185–191.

4.2 A TSH IFMA using an Ir(bipy)$_2$diphenyl phenanthroline/antibody conjugate as the fluorescent-labelled antibody Materials TSH antigen anti-TSH moncolonal antibodies 96-well microtitre plates NUNC 0.25M TRIS/HCl pH 8.5 buffer containing 2% BS. (BS= Heat inactiveated bovine serum)

0.1M Glycine/yCl pH 2.5 buffer 0.05M bicarbonate (sodium)

Wash buffer 0.1M acetate/citrate pH 60 containing 5 mM EDTA, 0.05% Tween 20.

Method

1. Plate coating

200 µl of a 50 mM bicarbonate solution containing 10 µg/ml anti-TSH monoclonal antibody were added to each well and incubated for 16–20 h at 37° C.

Th wells were washed once in the above bicarbonate solution containing 0.2% BSA and 0.1% lactose and left in this solution for 30 mins. Finally, the plates were washed in 50 mM bicarbonate, tapped dry, air dried, sealed and stored at 4° C. to use.

2. Assay

The Iridium-labelled monoclonal antibody was used at 10 μg/ml in 0.25M tris/HCl pH 8.5 and 2% bovine serum.

TSH antigen was used at 500, 250, 100, 50, 25, 0 mU/L diluted in the above tris buffer. 5 replicates were run per antigen point.

0.1 ml of the TSH standard was added to each well and reacted at room temperature for 30 min with shaking. The wells were washed three times in the wash buffer and tapped dry. 0.2 ml of the labelled antibody was then added to each well and reacted for 1 hr at room temperature with shaking. Unbound label was washed off with three washes in wash buffer and the plates tapped dry.

The assay products were eluted off the wells by the addition of 0.2 ml of 0.1M glycine-HCl pH 2.4 for 30 minutes.

The five replicates of each antigen point were pooled and fluorescence measured.

Results

A variable response in fluorescence intensity was detected with doses of TSH up to 500 mU/L.

It will be understood that the invention is described above by way of example only and modifications of detail may be made within the scope of the invention.

I claim:

1. A metal-labeled binding partner comprising a binding partner covalently bonded to a luminescent iridium complex, wherein said iridum complex is $Ir(bipy)_2$ (4'-[1,10-phenanthroline)]-phenoxy-acetic acid)$^{3+}$.

2. A metal-labeled binding partner comprising a binding partner covalently bonded to a luminescent iridium complex, wherein said iridium complex is $Ir(bipy)_2$ (4"-carboxybenzyl-4'-[4(1,10-phenanthroline)]-phenyl ether$^{3+}$.

3. A metal-labeled binding partner comprising a binding partner covalently bonded to a luminescent iridium complex, wherein iridium complex is $Ir(bipy)_2$ (4,7-diphenyl-1,10-phenanthroline)$^{3+}$.

4. A metal-labeled binding partner comprising a binding partner covalently bonded to a luminescent iridium complex, wherein said iridium complex is $Ir(bipy)_2$ (2,2'-biquinoline)$^{3+}$.

5. A metal-labeled binding partner comprising a binding partner covalently bonded to a luminescent iridium complex, wherein said iridium complex is $Ir(phen)_2$ (4'-[4-(1,10,10-phenanthroline)]-phenoxy-acetic acid)$^{3+}$.

* * * * *